(12) United States Patent
Zhao et al.

(10) Patent No.: US 10,870,680 B2
(45) Date of Patent: Dec. 22, 2020

(54) METHODS OF REDUCING NEURONAL INJURY OR TOXICITY IN EPILEPSY, ALZHEIMER'S DISEASE OR PARKINSON'S DISEASE USING A SCORPION VENOM HEAT-RESISTANT SYNTHETIC PEPTIDE (SVHRSP)

(71) Applicant: DALIAN MEDICAL UNIVERSITY, Liaoning (CN)

(72) Inventors: Jie Zhao, Liaoning (CN); Shao Li, Liaoning (CN); Wanqin Zhang, Liaoning (CN)

(73) Assignee: DALIAN MEDICAL UNIVERSITY, Liaoning (CN)

( * ) Notice: Subject to any disclaimer, the term of this patent is extended or adjusted under 35 U.S.C. 154(b) by 0 days.

(21) Appl. No.: 16/573,495

(22) Filed: Sep. 17, 2019

(65) Prior Publication Data

US 2020/0002381 A1  Jan. 2, 2020

Related U.S. Application Data

(60) Division of application No. 15/800,802, filed on Nov. 1, 2017, now Pat. No. 10,442,837, which is a continuation-in-part of application No. PCT/CN2016/112078, filed on Dec. 26, 2016.

(30) Foreign Application Priority Data

Aug. 8, 2016  (CN) .......................... 2016 1 0645111

(51) Int. Cl.

| | | |
|---|---|---|
| *A61K 38/00* | (2006.01) | |
| *C07K 7/00* | (2006.01) | |
| *A61P 25/28* | (2006.01) | |
| *A61K 38/10* | (2006.01) | |
| *A61K 35/646* | (2015.01) | |
| *A61P 25/08* | (2006.01) | |
| *A61P 25/14* | (2006.01) | |
| *A61P 25/00* | (2006.01) | |
| *C07K 14/435* | (2006.01) | |
| *C07K 7/08* | (2006.01) | |
| *A61P 25/16* | (2006.01) | |
| *A61K 47/64* | (2017.01) | |
| *A61K 47/68* | (2017.01) | |
| *A61P 29/00* | (2006.01) | |
| *A61P 25/02* | (2006.01) | |
| *A61P 25/04* | (2006.01) | |
| *A61K 38/02* | (2006.01) | |

(52) U.S. Cl.
CPC .............. *C07K 7/08* (2013.01); *A61P 25/08* (2018.01); *A61P 25/16* (2018.01); *A61P 25/28* (2018.01); *C07K 14/43522* (2013.01); *A61K 38/00* (2013.01); *A61K 38/02* (2013.01); *A61K 47/6415* (2017.08); *A61K 47/6817* (2017.08); *A61K 2300/00* (2013.01); *A61P 25/02* (2018.01); *A61P 25/04* (2018.01); *A61P 29/00* (2018.01); *C07K 14/43504* (2013.01); *C07K 14/43518* (2013.01); *C12N 2310/3513* (2013.01)

(58) Field of Classification Search
CPC ............ A61K 2300/00; A61K 47/6415; A61K 47/6817; C07K 14/43522; C07K 7/08; C07K 14/43518; A61P 25/08; A61P 25/16; A61P 25/28; A61P 29/00; C12N 2310/3513
See application file for complete search history.

(56) References Cited

U.S. PATENT DOCUMENTS

| | | | | |
|---|---|---|---|---|
| 2003/0235902 A1* | 12/2003 | Ishikawa | .............. | C12N 9/0036 435/252.3 |
| 2005/0164350 A1* | 7/2005 | Ishikawa | .............. | C12N 9/0036 435/69.1 |
| 2007/0191272 A1* | 8/2007 | Stemmer | .............. | C07K 14/001 435/7.1 |
| 2007/0212703 A1* | 9/2007 | Stemmer | .............. | C07K 14/001 435/6.16 |

FOREIGN PATENT DOCUMENTS

| | | |
|---|---|---|
| CN | 1324621 A | 12/2001 |
| CN | 101284870 A | 10/2008 |
| CN | 101450966 A | 6/2009 |
| CN | 103304630 A | 9/2013 |
| CN | 104341495 A | 2/2015 |

OTHER PUBLICATIONS

Swerdlow, Clin. Interv. Ageing 2007; 2:347-359.*
Atwood et al., J. Alzheimer's Disease; 2015; 47:33-47.*
Anger. Neurotoxicology 1991. 12: 403-13.*
Tayebati. Mech. Ageing Dev. 2006. 127: 100-8.*
Sarter. Neurosci. and Biobehavy. Rev. 2004. 28: 645-650.*
Falkenburger et al., J. Neural. Transm, 2006; 70:261-268.*
The fact sheet of refractory seizure or epilepsy retrieved from the web site Johns Hopkins Medicine Health Library.*
French, Epilepsy Curr. 2006; 6:177-180.*
Kang et al., Austin J. Cerebrovasc.Dis. Stroke. 2014; 1: 1-11.*

(Continued)

*Primary Examiner* — Chang-Yu Wang
(74) *Attorney, Agent, or Firm* — Novick, Kim & Lee, PLLC; Allen Xue

(57) ABSTRACT

A scorpion venom heat-resistant synthetic peptide (SVHRSP) contains an amino acid sequence of SEQ ID NO 1. One or more amino acids the amino acid sequence can be substituted or deleted. A pharmaceutical composition that contains the SVHRSP has numerous applications. The pharmaceutical composition can be used to protect neuronal cell against amyloid beta-induced toxic effects, or to inhibit the sodium channel current of a hippocampal neuronal cell, or to protect a neuronal cell against NMDA-induced injury. It may also promote the formation of a pluripotent neural stem cell from a type II astrocyte, or treats a subject, such as a human, having epilepsy, Alzheimer's disease, or Parkinson's disease.

12 Claims, 14 Drawing Sheets
Specification includes a Sequence Listing.

(56) References Cited

OTHER PUBLICATIONS

Henstridge et al., Nat. Rev. Neurosci. 2019; 20: 94-107.*
Kandratavicius et al., Neurospyschia. Dis. & Treatment; 2014; 10:1693-105.*
Moore et al. Annu. Rev. Neurosci. 2005; 28:57-87.*
Jagmag et al., Front. Neurosci. 2016; 9:503. Doi:10.3389/fnins.2015.00503.*
Potashikin et al., Parkinson's Disease, 2011; 658083; doi:104061/2011/658083.*
Jackson-Lewis et al., Parkinsonims and Related Dis. 2012; 18S1:S183-S185.*
Kwan et al., Epilepsia; 2009; 50:57-62.*
De La Salud Bea, Roberto et al. "Synthesis of analogs of peptides from Buthus martensii scorpion venom with potential antibiotic activity", Elsevier, 2015, p. 228-232, vol. 68, Elsevier, Department of Chemistry, Rhodes College, 2000 North Parkway, Memphins, TN 38112, USA.
Burgess, Wilson H. et al. "Possible Dissociation of the Heparin-binding and Mitogenic Activities of Heparin-binding (Acidic Fibroblast) Growth Factor-I from Its Receptor-binding Activities by Site-directed Mutagenesis of a Single Lysine Residue", The Journal of Cell Biology, Nov. 1990, p. 2129-2138, vol. 111.
Bowie, James U. et al. "Deciphering the Message in Protein Sequences: Tolerance to Amino Acid Substitutions" Science, New Series, vol. 247, No. 4948, Mar. 16, 1990, p. 1306-1310.
Pawson, Tony et al. "Assembly of Cell Regulatory Systems Through Protein Interaction Domains", Science, Apr. 18, 2003, p. 445-452, vol. 300.
Alaoui-Ismaili, Hicham Moulay et al. "Design of second generation therapeutic recombinant bone morphogenetic proteins", Cytokine & Growth Factor Reviews, 2009, vol. 20, p. 501-507.
Guo, Haiwei et al. "Protein tolerance to random amino acid change", PNAS, Jun. 22, 2004, vol. 101, No. 25, p. 9205-9210.
Zeng, Xian-Chun et al. "Cloning and Characterization of a Novel cDNA Sequence Encoding the Precursor of a Novel Venom Peptide (Bmkbpp) Related to a Bradykinin-Potentiating Peptide from Chinese Scorpion Buthus martensii Karsch", IUBMB Life, 2000, p. 207-210, vol. 49.
Zeng, Xian-Chun et al. "Scorpion Venom Peptides without Disulfide Bridges", IUBMB Life, 2005, vol. 57, No. 1, p. 13-21.
Zeng, Xian-Chun et al. "Characterization of BmKbpp, a multifunctional peptide from the Chinese scorpion Mesobuthus martensii Karsch: Gaining insight into a new mechnism for the functional diversification of scorpion venom peptides", Peptides, 2012, p. 44-51, vol. 33.
Zhao, Ruiming et al. "Comparative venom gland transcriptome analysis of the scorpion Lychas muconatus reveals intraspecific toxic gene diversity and new venomous components", BMC Genomics, 2010, p. 1-15, Bio Med Central.
Verano-Braga, Thiago et al. "Moving Pieces in a Venomic Puzzle: Unveiling Post-translationally Modified Toxins from Tityus serrulatus", Journal of Proteome Research, 2013, p. 3460-3470, vol. 12.
Kozminsky-Atias, Adi et al. "Assembling an arsenal, the scorpion way", BMC Evolutionary Biology, 2008, p. 1-13, vol. 333, BioMed Central, Department of Life Sciences, Ben-Gurion Uni. of the Negev, Beer-Sheva 84105 and Israel and Zlotowski for Neuroscience, Ben-Gurion University of the Negev, Beer-Sheva 84105, Israel doi:10.1186/1471-2148-8-333.
Almaaytah, Ammar et al. "Scorpion venom peptides with no disulfide bridges: A review", Peptides, 2014, vol. 51, p. 35-45.

* cited by examiner

A

B

C

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthesized

<400> SEQUENCE: 1

```
Lys Val Leu Asn Gly Pro Glu Glu Ala Ala Ala Pro Ala Glu
1               5                   10                  15
```

METHODS OF REDUCING NEURONAL INJURY OR TOXICITY IN EPILEPSY, ALZHEIMER'S DISEASE OR PARKINSON'S DISEASE USING A SCORPION VENOM HEAT-RESISTANT SYNTHETIC PEPTIDE (SVHRSP)

CROSS-REFERENCING

This application is a divisional application of U.S. application Ser. No. 15/800,802, filed on Nov. 1, 2017 (now U.S. Pat. No. 10,442,837), which is a continuation-in-part of international Application No. PCT/CN2016/112078, filed Dec. 26, 2016, which claims priority to Chinese patent Application No. 201610645111.7, filed Aug. 8, 2016.

INCORPORATION OF SEQUENCE LISTING

This application contains a sequence listing submitted in Computer Readable Form (CRF). The CFR file contains the sequence listing entitled "PA128-0041DIV-seq.txt", which was created on Sep. 11, 2019, and is 615 bytes in size. The information in the sequence listing is incorporated herein by reference in its entirety.

TECHNICAL FIELD

The present invention belongs to the field of research and development of polypeptide medicines, and more particularly relates to applications of an amino acid sequence of scorpion venom heat-resistant peptide (SVHRP) obtained from scorpion venom of Chinese medicine *Buthus martensii* Karsch and its synthetic product scorpion venom heat-resistant synthetic peptide (SVHRSP) in the treatment of epilepsy, Alzheimer's disease and Parkinson's disease.

BACKGROUND ART

The clinical symptoms of Parkinson's Disease (PD) raise due to a severe reduction in the level of striatal dopamine (DA) neurotransmitters resulting from DA neuronal injury of the substantia nigra of midbrain. The PD oxidative stress theory is proposed due to DA oxidative stress; the theory of free radicals is an important mechanism of DA neuronal injury of substantia nigra pars compacta (NCs). The antioxidant therapy is a well-known effective therapeutic regimen at present.

The Chinese medicine *Buthus martensii* Karsch (BmK), modern medical studies have proved that scorpion venom (SV), which is released from the scorpion tail venom gland, is rich in toxins. These toxins can be divided into neurotoxins and cytotoxins according to their toxin mechanisms. The neurotoxins are divided into long-chain scorpion toxins (containing 60-70 amino acid residues) and short-chain scorpion toxins (containing 30-40 amino acid residues). The long-chain scorpion toxins are mainly targeted to voltage-dependent Na+ channels on neural excitable membrane, and the short-chain scorpion toxins can act on Ca2+ channels, K+ channels or Cl− channels. The scorpion toxins have been widely used in development of tool drugs and antitoxins of membrane ion channels. Scorpio is a traditional Chinese medicine. So far, China has separated and purified scorpion toxins with anti-tumor, anti-pain, antiepileptic, anti-thrombosis, anti-inflammatory, anti-rheumatic and anti-bacterial functions from BmK scorpion venom. The toxicity of scorpion venom is second only to snake venom. The national invention patent CN1324621 has confirmed the effectiveness and the safety after technology treatment of the venom, i.e. the scorpion venom, released from the scorpion tail venom gland (the medicinal part) of the natural medicine scorpio on refractory epilepsy (RE). The national invention patent application (Application No. 201310330290.1) discloses the removal of heat-labile and heat-resistant toxic components from the SV of BmK to obtain a safer SVHRP extract. The polypeptide has common action targets and respective specific effects in prevention and treatment of refractory epilepsy (RE), Parkinson's Disease (PD) and Alzheimer's disease (AD). But the SVHRP extract is low in peptide obtainment rate, and therefore, the obtainment of the chemically synthesized SVHRP is a key link to determine whether this original research and development result can be transformed and industrial production.

SUMMARY OF THE INVENTION

The present invention aims to provide a chemically synthetic SVHRP with a therapeutic effect and applications thereof. The present application mainly comprises: determining the amino acid sequence of the SVHRP, and carrying out solid-phase chemical synthesis according to the amino acid sequence as well as pharmacological activity and safety detection of the SVHRSP.

The amino acid sequence of the SVHRSP of the present invention is as follows:

SEQ ID No.1: (N-terminal) Lys-Val-Leu-Asn-Gly-Pro-Glu-Glu-Glu-Ala-Ala-Ala-Pro-Ala-Glu (C-terminal). The SVHRSP is a synthetic active polypeptide containing 15 amino acid residues and having a molecular weight of 1524 Da.

According to the SVHRSP of the present invention, firstly the amino acid sequence of the SVHRP is obtained from the traditional Chinese medicine BmK scorpion venom: mainly comprising the following steps: animal experiments prove that a sample (xiedu 20160112-peptide summary) has significant prevention and treatment effects on refractory epilepsy, Parkinson's disease and senile dementia; secondly the sample is treated with LaGm composite and subjected to repeated fast magnetic separation, and then subjected to nano-liter reversed-phase chromatography and electrospray ionization mass spectrometry (nanoLC-ESI-MS) integrated mass spectrometry parallel experiment to detect out the amino sequence of the SVHRP; and finally, SVHRSP is prepared by solid-phase chemical synthesis, chromatography purification and mass spectrometry identification. The amino acid sequence of the SVHRSP is as shown in SEQ ID NO.1, and it keeps pharmacological activity and safety as well as various biological activities of the SVHRP.

A method for preparing the scorpion venom heat-resistant synthetic peptide of the present invention is as follows:

1. Determination of Amino Acid Sequence of the SVHRP (1) freeze-dried powder of BmK scorpion venom is redissolved and centrifuged to obtain supernatant, and the supernatant is heated at 100° C. in water bath, then taken out and centrifuged to obtain supernatant, i.e. a scorpion venom heat-resistant component extract. The scorpion venom heat-resistant component extract is subject to centrifugal ultrafiltration with centrifugal ultrafiltration tubes with filtering members having molecular weights of 50 kDa and 30 kDa successively to obtain an upper bath solution, i.e. a SVHRP extract. The sample is roughly fractionated with a Superdex Peptide 10/300GL molecular sieve column (Optimum Separation range (peptides) M, 100-7000 Da) (see FIG. 1), and is finely fractionated with HPLC (see FIG. 2), the chromatographic conditions being as follows:

a chromatographic column: Zorbax SB-C18 4.6*250 5 μm (AgilentUSA); a mobile phase comprises solution A and solution B. Solution A contains acetonitrile and water with a volume ratio of 2:98 and an extra 0.1% of trifluoroacetic acid was added; whereas solution B contains acetonitrile and water with a volume ratio of 98:2 and an extra 0.08% of trifluoroacetic acid was added. The procedure of elution is performed successively through mobile phase containing 0-40% solution B with a capacity of approximately 3-6 column volumes, 40-100% solution B with a capacity of approximately 0.5-1 column volume, and 100% solution B with a capacity of approximately 1-3 column volumes (CV); a flow rate: 0.8 ml/min; a UV detector having detection wavelength: 280 nm/258 nm/214 nm.

(2) the sample finely fractionated with HPLC in (1) of step 1 is freeze-dried. The freeze-dried polypeptide sample is redissolved in Nano-RPLC Buffer A; online Nano-RPLC liquid chromatography is performed in an Eksigentnano LC-Ultra™ 2 D System (AB SCIEX). The dissolved sample is loaded onto a C18 pre-column (100 µm×3 cm, C18, 3 µm, 150 Å) at a flow rate of 2 µL/min, and rinsed and desalted at a constant flow rate for 10 min. The mass spectrometry is performed using a TripleTOF 5600 system (AB SCIEX) combined with a nano-liter spray III ion source (AB SCIEX, USA), And original wiff spectrum files collected from the mass spectrometry is subject to data processing using Protein Pilot Software v. 4.5 (AB SCIEX, USA) to obtain a SVHRP, see sequence table SEQ ID No. 1.

2. Preparation of SVHRSP by Solid-Phase Chemical Synthesis (1) The polypeptide synthesis technology is used to obtain target molecules in accordance with the amino acid sequence of the SVHRP by means of a directional formation method of amido bonds. The solid-phase synthesis comprises: connecting a carboxyl of an amino acid of a bulk drug in the form of a covalent bond with a solid-phase carrier (Fmoc resin), and then performing an acylation reaction on an amino of this amino acid as a synthesis starting point with a carboxyl of amino acid (amino-protected) adjacent thereto to form a peptide bond. The amino of the resin peptide containing these two amino acids is then deprotected and reacted with the carboxyl of the next amino acid, and the process is repeated until the target peptide is formed.

(2) High Performance Liquid Chromatography (HPLC) purification: a polypeptide synthesis process may produce some hybrid peptides (see FIG. 6) similar to the target peptide in structure a polypeptide synthesis process, such as diastereomers produced due to racemization of amino acids, deletion peptide produced due to un-connected part of amino acids and broken peptide produced due to the breakage of a peptide bond. The chromatographic conditions are as follows: chromatographic column is Inertsil ODS-SP 4.6 mm*250 mm, acetonitrile contains 0.1% trifluoroacetic—water contains 0.1% trifluoroacetic, and a UV detector having a detection wavelength of 214 nm.

(3) The amino acid sequence, see the sequence table SEQ ID No. 1, of the SVHRSP is detected out by performing structural verification and retrieval analysis on the synthetic polypeptide by mass spectrometry.

The effect of the SVHRSP of the present invention on the learning and memory of AD mice is detected by Morris water maze test, and the result shows that the SVHRSP has a effect in the spatial learning and memory ability of the AD mice. Aβ neurotoxicity is measured by nematode chemotaxis assay, and the result shows that the SVHRSP could protect neurons against AP-induced toxic effects and improve the abnormal chemotaxis behavior induced by neuronal AP expression. The prevention and treatment effects of the SVHRSP on the intractable epilepsy pilocarpine model rats are observed, and the experimental result shows that the SVHRSP has a significant control effect on chronic model epileptic episodes of lithium-pilocarpine epilepsy rats and the number of episodes can be reduced significantly. The inhibitory effects of the SVHRSP on the sodium current of primary cultured neurons is observed, and the experimental result shows that the SVHRSP could significantly inhibit the sodium channel current of primary cultured hippocampal neurons; and have a protection effect in SH-SY5Y cell injury induced by NMDA. The effects of the SVHRSP on type II astrocytes are observed, and the result shows that the SVHRSP could promote the reprogramming (dedifferentiation) of type II astrocytes into intracerebral endogenous neural stem cells. The ability of SVHRSP to remove active oxygen produced inside SH-SY5Y cells induced by 6-OHDA is detected by measuring ROS in the cells, and the result shows that SVHRSP can significantly remove intracellular ROS and have an inhibitory role in PD oxidative stress. The pharmacological safety and pharmacokinetic ratio of the SVHRSP is more than 2000/0.05=40,000 times. The administration dose of the intraperitoneal injection of Kunming mice is as high as 2000 mg/kgBW and no toxic reaction is observed, which shows the application prospect of the SVHRSP as a new antiepileptic, anti-Alzheimer's disease and anti-Parkinson's disease drug.

This disclosure further discloses a scorpion venom heat-resistant synthetic peptide (SVHRP) comprising an amino acid sequence of SEQ ID NO 1. In one of the embodiments of the SVHRP, in the amino acid sequence, one or more amino acids are substituted or deleted.

This disclosure also discloses a pharmaceutical composition that contains the SVHRP. In a further embodiment, a method of protecting a neuronal cell against amyloid beta-induced toxic effects include a step of contacting the neuronal cell with an effective amount of the pharmaceutical composition have the SVHRP.

In addition, this disclosure provides a method of inhibiting the sodium channel current of a hippocampal neuronal cell, which includes the step of contacting the hippocampal neuronal cell with an effective amount of the pharmaceutical composition containing the SVHRP.

Still, by contacting the neuronal cell with an effective amount of the pharmaceutical composition containing SVHRP, one may protect a neuronal cell against NMDA-induced injury.

In another embodiment, a method of promoting the formation of a pluripotent neural stem cell from a type II astrocyte includes a step of contacting the type II astrocyte with an effective amount of the pharmaceutical composition containing SVHRP.

Administering to a subject a therapeutically effective amount of the pharmaceutical composition containing SVHRP also can be effective in treating the subject having epilepsy or having Alzheimer's disease, or having Parkinson's disease.

DETAILED DESCRIPTIONS OF THE PREFERRED EMBODIMENTS

The following embodiments further illustrate the content of the present invention without limiting it.

Embodiment 1

Determination of Amino Acid Sequence of the Scorpion Venom Heat-Resistant Peptide (1) Freeze-dried powder of BmK scorpion venom from Yichang city, Henan Province is dissolved with tri-distilled water, and centrifuged to obtain supernatant, i.e. BmK scorpion venom extract. The BmK scorpion venom extract is filled in heat-resistant plastic pipes with covers, put in a homothermal water bath and heated at 100° C., taken out after 4 h, naturally cooled to room temperature, centrifuged at a high speed to obtain supernatant, i.e. a scorpion venom heat-resistant component extract; the scorpion venom heat-resistant component extract is subject to centrifugal ultra-filtration with centrifugal ultrafiltration tubes with filtering members having molecular weights cutoff of 50 kDa and 30 kDa successively to obtain an upper bath solution, i.e. a scorpion venom heat-resistant polypeptide extract.

Figure 1:
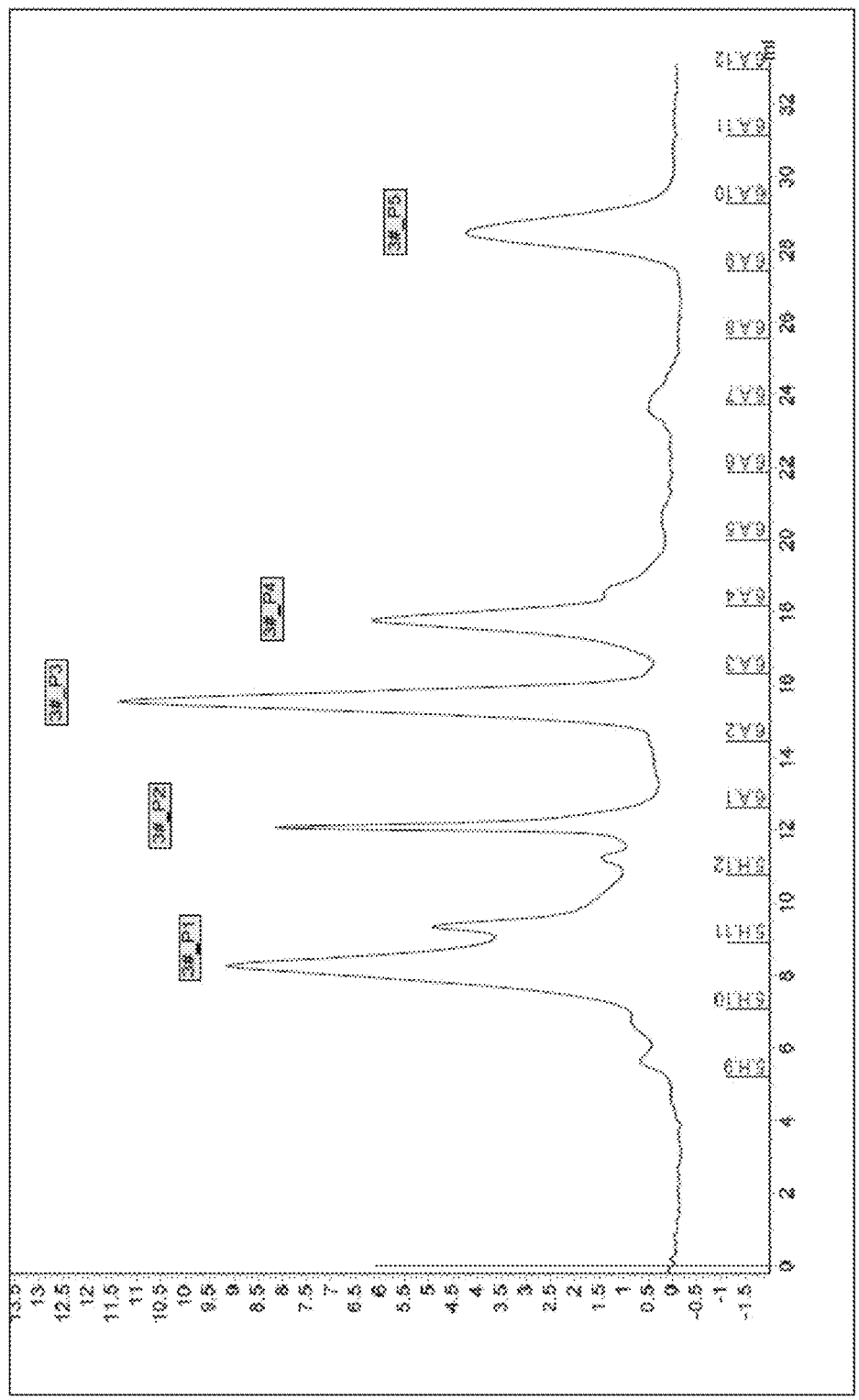
FIG. 1 is a gel filtration chromatography chromatogram of a scorpion venom heat-resistant peptide compound purified from *Buthus martensii* Karsch (BMK)
Figure 2:
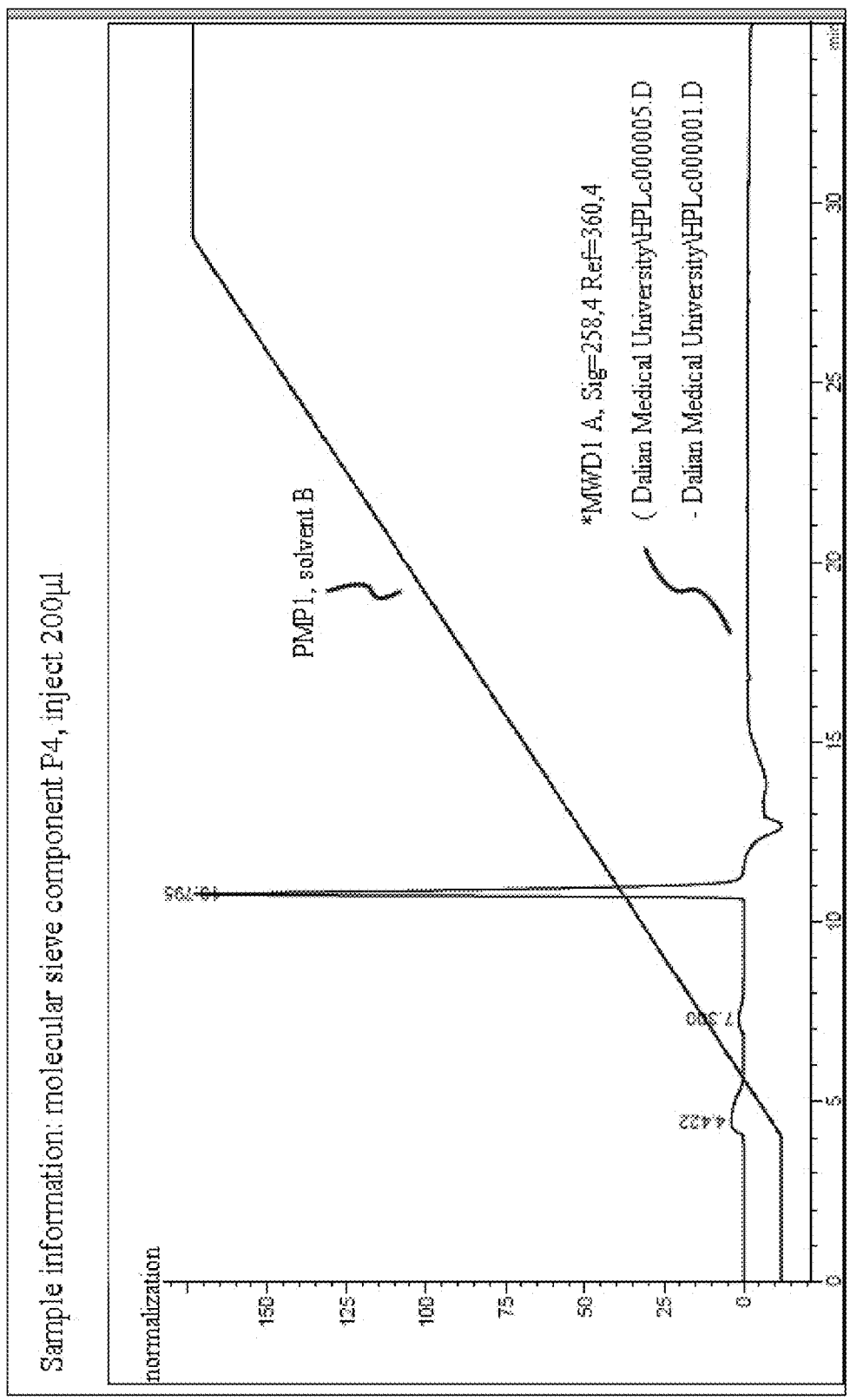
FIG. 2 is a RP-HPLC chromatogram of the scorpion venom heat-resistant peptide compound purified from *Buthus martensii* Karsch (BMK)
Figure 3:
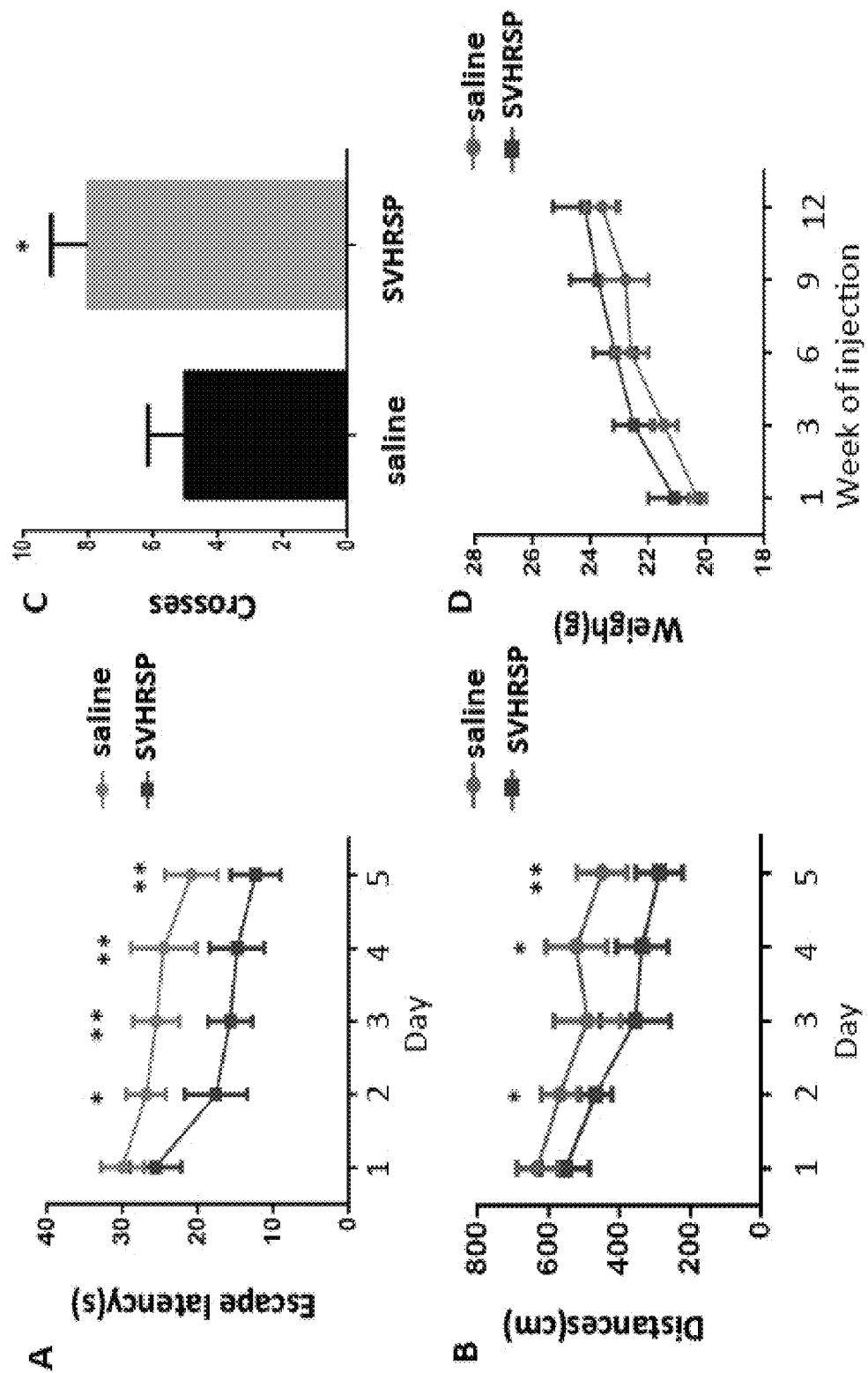
FIG. 3 shows the effect of the SVHRSP on the spatial learning and memory ability of Alzheimer's disease (AD) mice detected by Morris water maze test.
Figure 4:
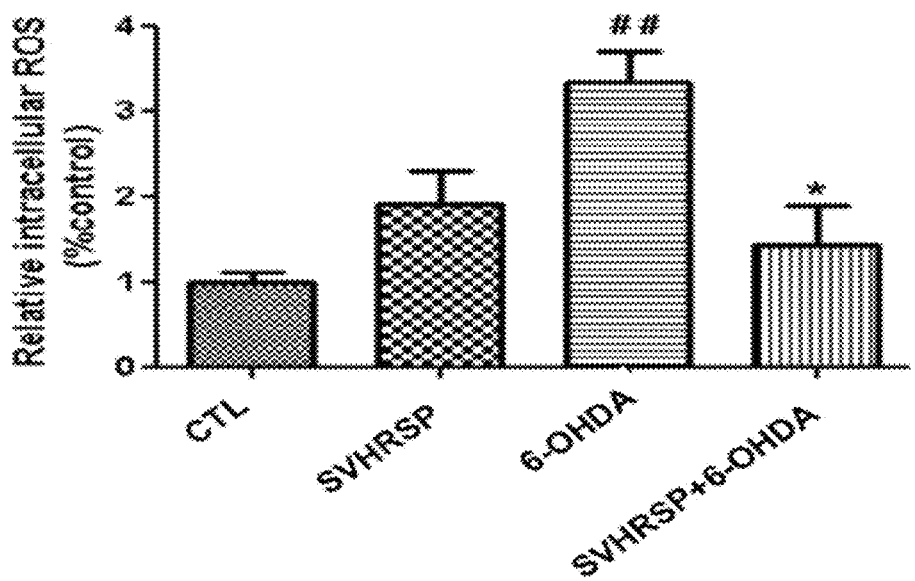
FIG. 4 shows the removal of ROS induced by a 6-OHDA PD cell model by the SVHRSP.
Figure 5:
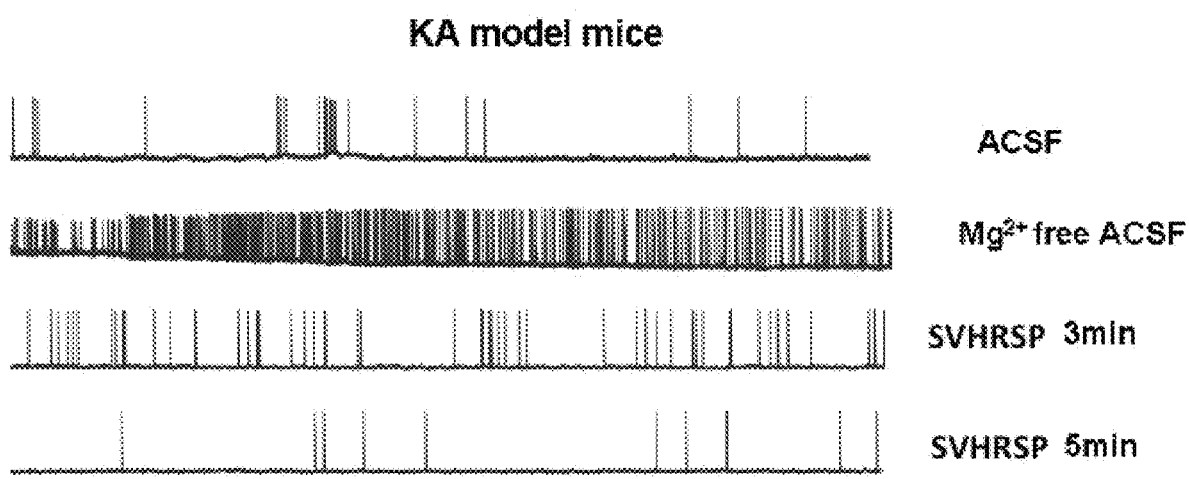
FIG. 5 shows that the SVHRSP inhibits epileptiform discharges of hippocampal slices using patch clamp technique.
Figure 6:
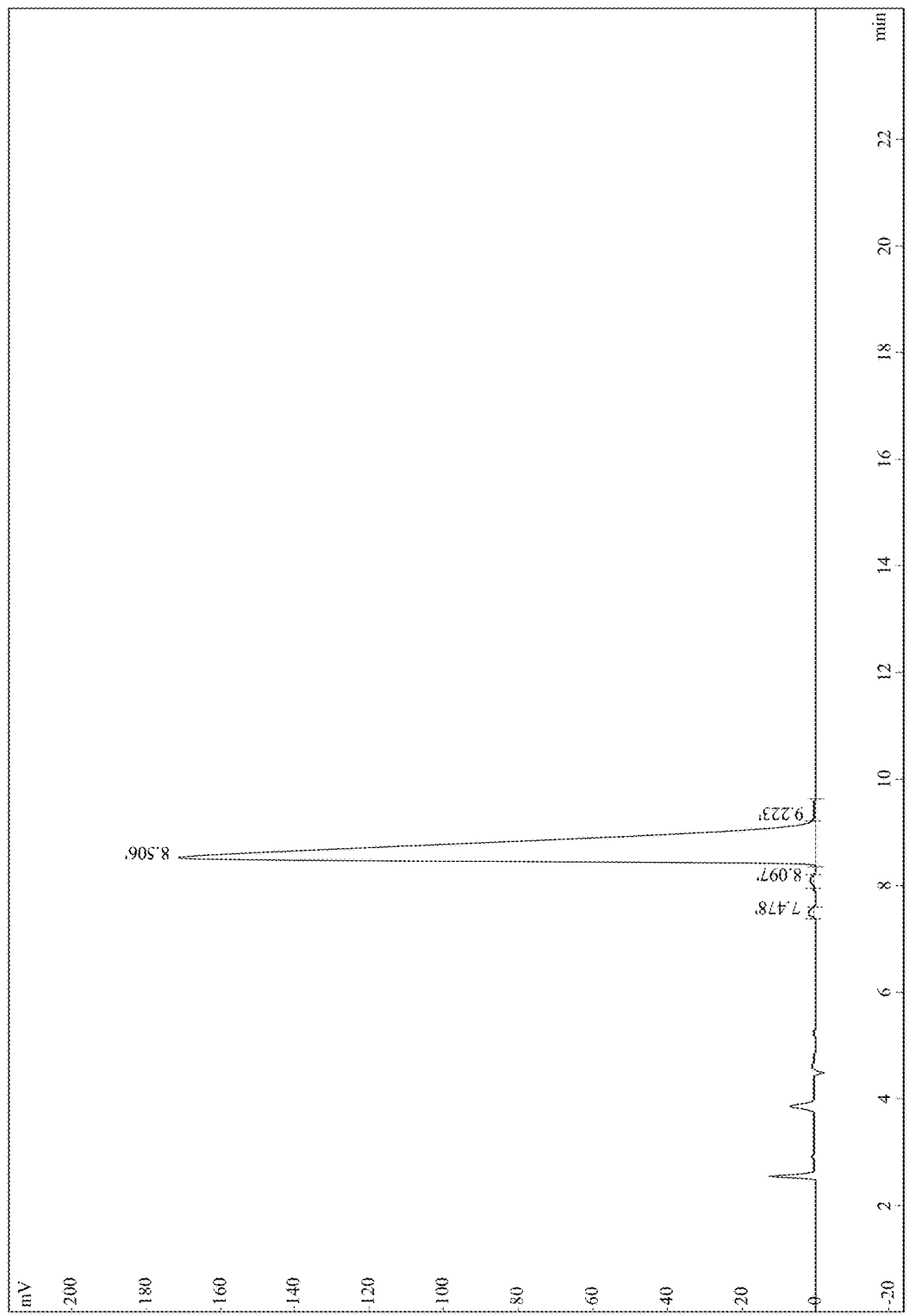
FIG. 6 is a reversed-high performance liquid chromatography (RP-HPLC) result of the SVHRSP.
Figure 7:
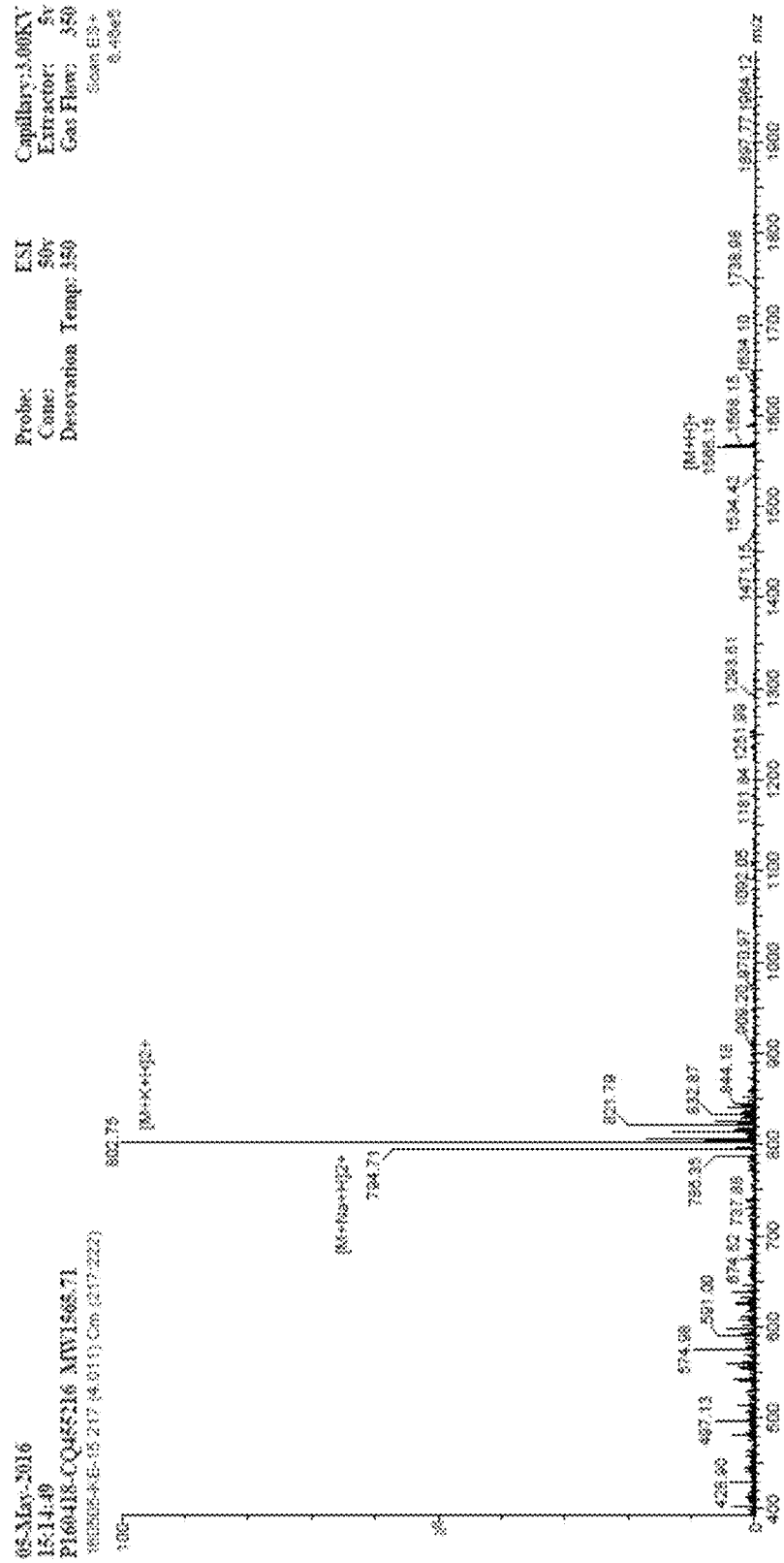
FIG. 7 is an MS identification result of the SVHRSP.
Figure 8:
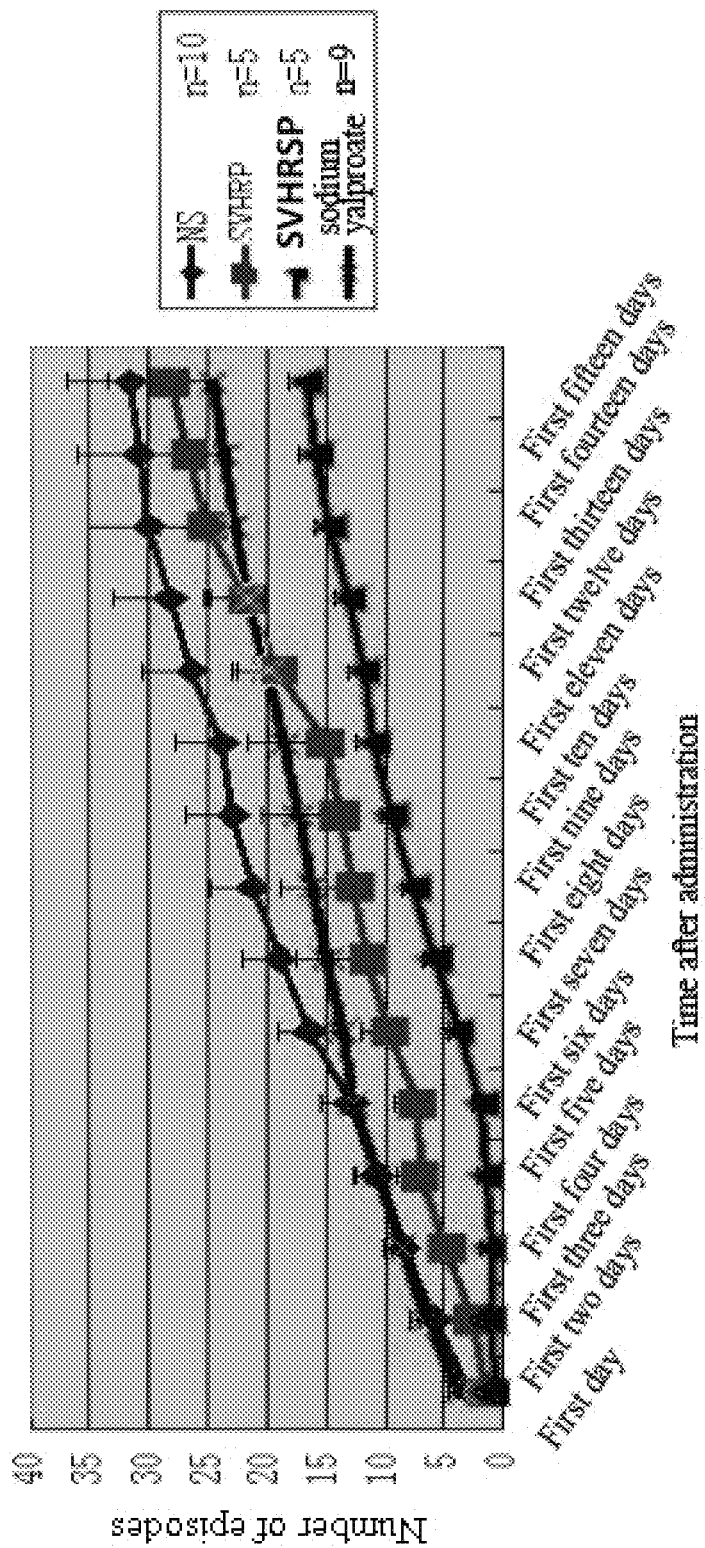
FIG. 8 shows an Inhibitory effect of the SVHRSP on behavior (recurrent episodes) of lithium-pilocarpine epilepsy model rats.
Figure 9:
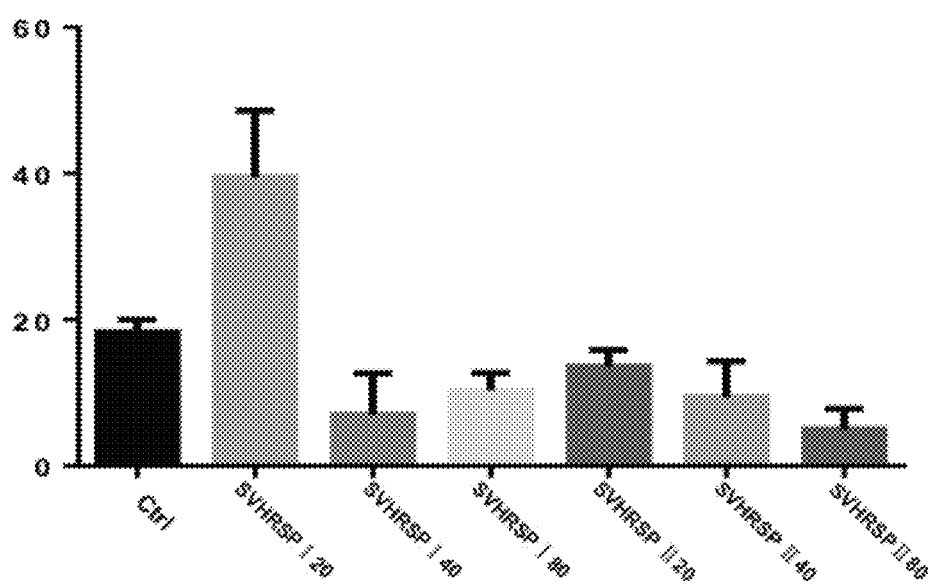
FIG. 9 shows the effect of the SVHRSP on the chemotaxis behavior of AD transgenic *Caenorhabditis elegans* CL2355.
Figure 10:
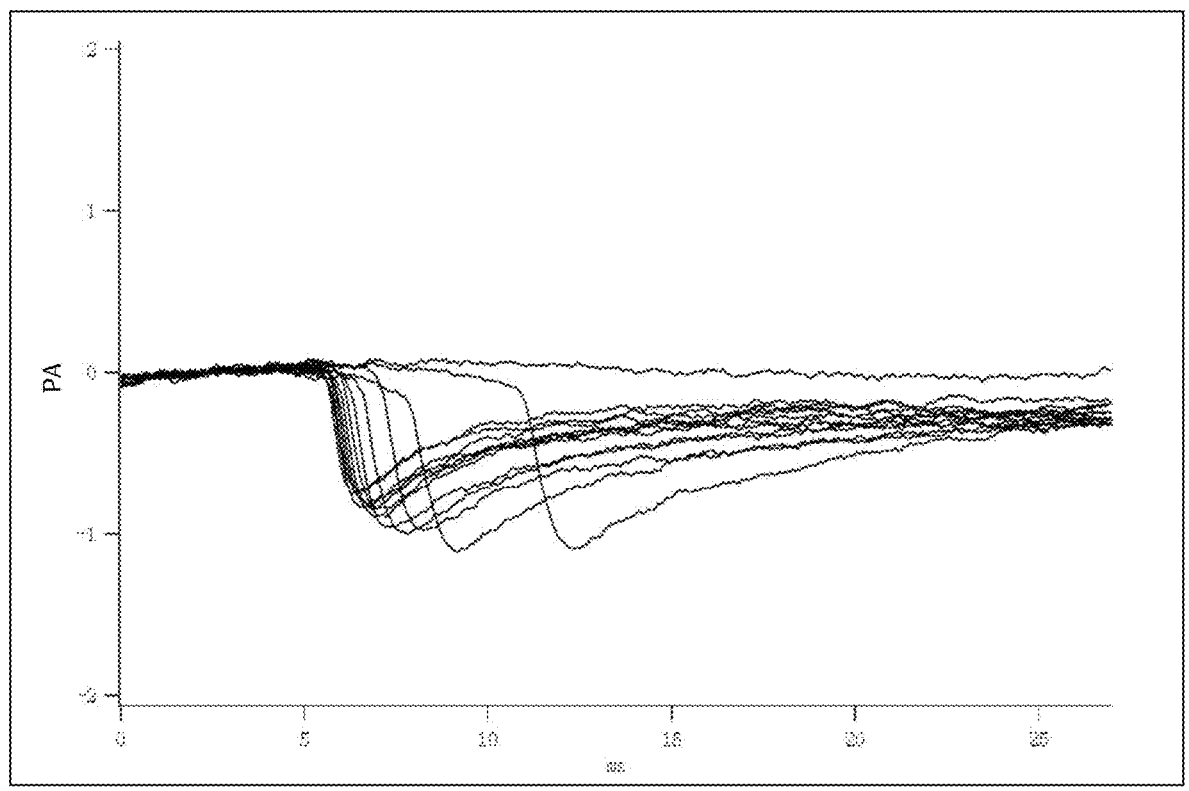
FIG. 10 shows the inhibitory effect of the SVHRSP on the sodium current of primary cultured neurons.
Figure 10:
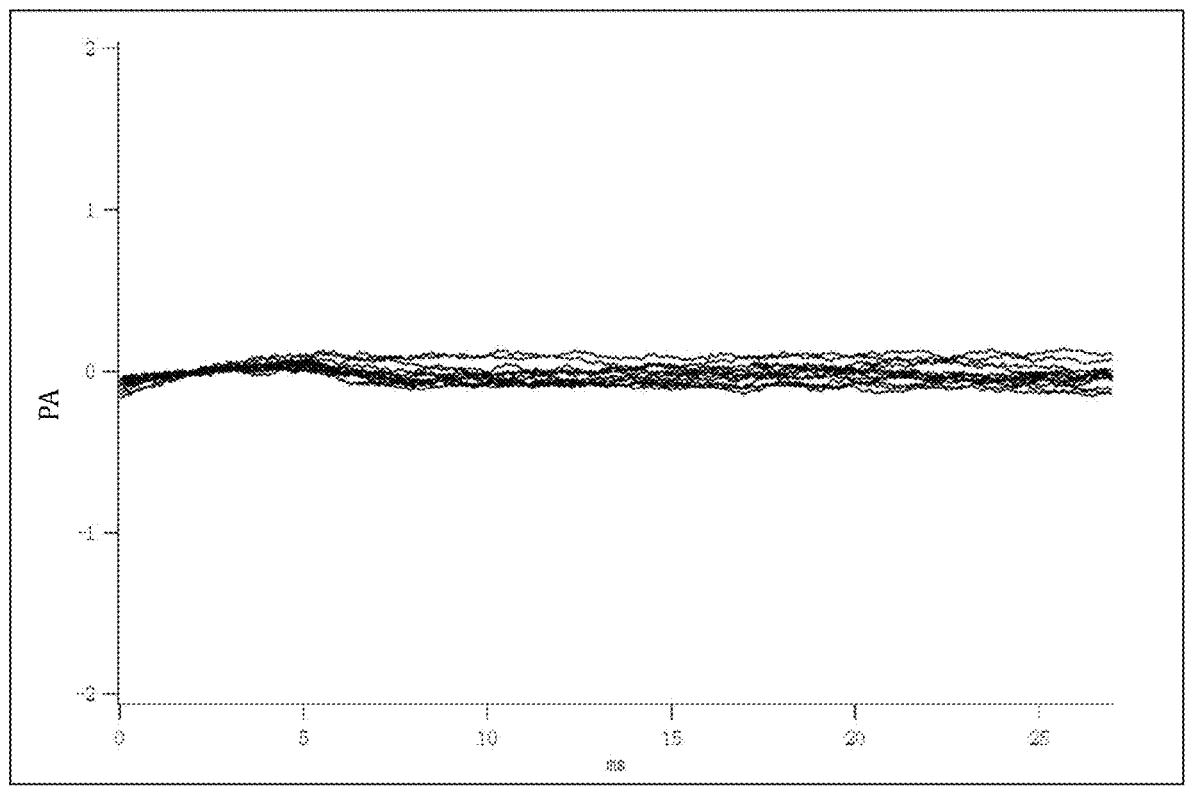
Figure 10:
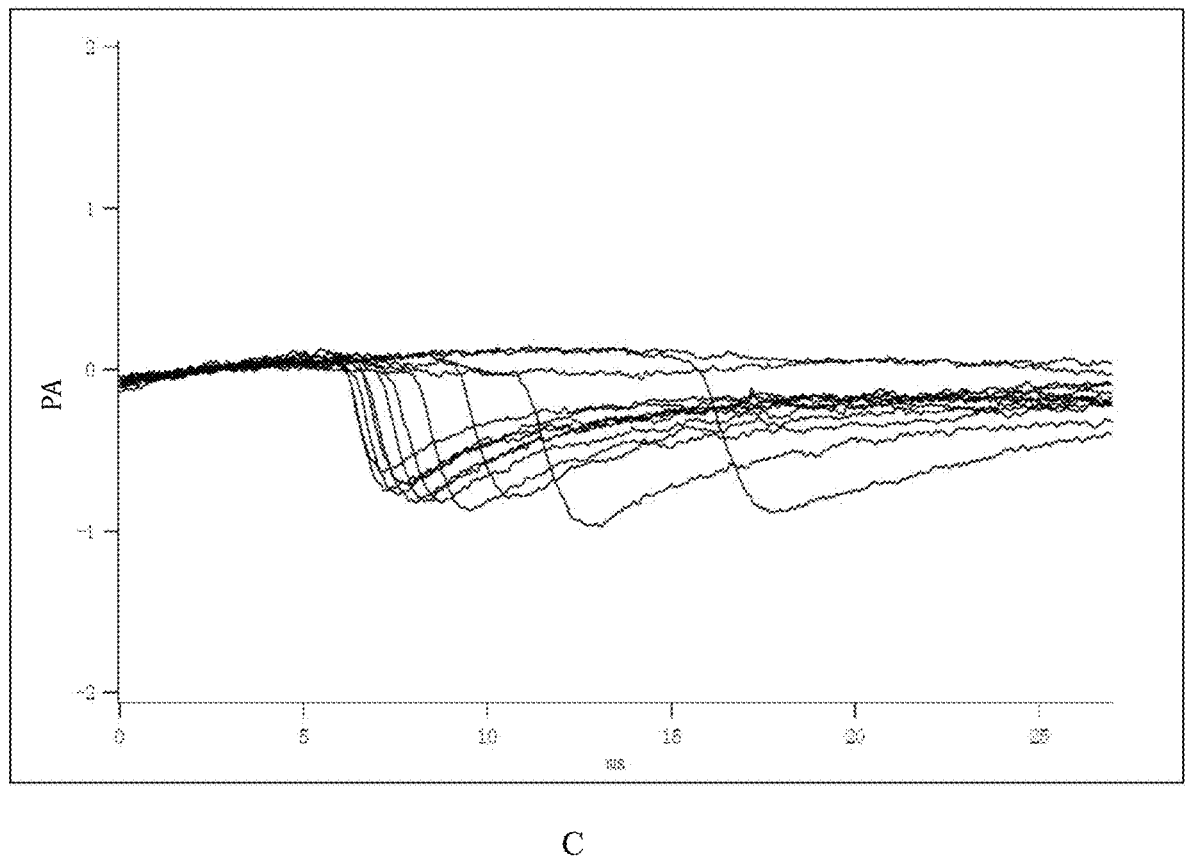

The scorpion venom heat-resistant polypeptide extract is roughly fractionated with a Superdex Peptide 10/300GL molecular sieve column (Optimum Separation range (peptides) M, 100-7000 Da) (see FIG. 1), and is finely fractionated with HPLC (see FIG. 2), the chromatographic conditions being as follows: a chromatographic column: Zorbax SB-C18 4.6*250 5 μm (Agilent. USA); a mobile phase: a solution A: acetonitrile/water: 2:98 (containing trifluoroacetic acid 0.1%); a solution B: acetonitrile/water: 98:2 (containing trifluoroacetic acid 0.08%); 0-40% B being about 3-6 column volumes, 40-100% B being 0.5-1 column volume, and 100% B being 1-3 column volumes (CV); a flow rate: 0.8 ml/min; a UV detector, detection wavelengths: 280 nm/258 nm/214 nm. Therefore, a purified scorpion venom heat-resistant polypeptide extract is prepared.

(2) 1.5 ml of purified scorpion venom heat-resistant polypeptide extract is taken, and centrifuged at 10000 rpm for 10 min to obtain supernatant. 30 mg/mL-LaGM composite is added to the supernatant according to the ratio that supernatant: 30 mg/mL-LaGM composite=50:1, sufficiently whirled for 2 min and then oscillated at 1000 r at room temperature for 10 min. The supernatant is removed by magnetic separation after being centrifuged at 10000 r for 5 min, and precipitate is added with 500 ul of water, sufficiently whirled for 1 min, oscillated for 5 min at room temperature, centrifuged at 10000 r for 5 min and then subjected to magnetic separation to remove supernatant, and the steps are repeated twice. The precipitate is added with eluent of 20 ul 80%+1% TFA, whirled for 1 min, oscillated for 5 min at room temperature, centrifuged at 10000 r for 5 min and subject to magnetic separation, then supernatant is collected, and these steps are repeated once; and then the collected supernatant is freeze-dried. The freeze-dried polypeptide sample separated from the magnetic material is dissolved in Nano-RPLC Buffer A, online Nano-RPLC liquid chromatography is performed in an Eksigentnano LC-Ultra™ 2 D System (AB SCIEX), the dissolved sample is loaded onto a C18 pre-column (100 μm×3 cm, C18, 3 μm, 150 Å) at a flow rate of 2 μL/min, and rinsed and desalted at a constant flow rate for 10 min. The analytical column is a C18 reversed-phase column (75 μm×15 cm C18-3 μm 120 Å, ChromXPEksigent), the gradient of the mobile phase B used in experiments is increased from 5% to 80% within 70 min. The mass spectrometry is performed using a TripleTOF 5600 system (AB SCIEX) combined with a nano-liter spray III ion source (AB SCIEX, USA), the spray voltage is 2.4 kV, the air curtain pressure is 30 Psi, the atomization pressure is 5 Psi, the heating temperature is 150° C., and the scanning time of primary TOF-MS single spectrum is 250 ms, 35 secondary spectras with a charge of 2+ to 8+ and a count per second being more than 100 are collected in each IDA cycle, the cumulative time for each secondary spectrum is 80 ms. Each cycle time is fixed to 2.5 seconds, the collision chamber energy setting is applied to all precursor ion collision induced dissociation (CID), and the dynamic exclusion is set to 11 seconds.

(3) Data Analysis Conditions

An original wiff spectrum file collected from mass spectrometry is subject to data processing and retrieval analysis using Protein Pilot Software v. 4.5 (AB SCIEX, USA), wherein a database is scorpions in a uniprot library, the retrieval method involves thorough analysis, and the false positive rate is controlled to 1% FDR. The SVHRSP is prepared, see sequence table SEQ ID No. 1 for its amino acid sequence.

The search results are shown in Table 1.

TABLE 1

NanoLC-ESI-MS combined MS parallel experiments in which an amino acid sequence of the SVHRP is detected out.

| Lot No | Amino Acid Sequence | Modifications | Disulfide bond | Molecular Weight Prec/Theor | Signal Intensity Precursor Signal |
|---|---|---|---|---|---|
| Xiedu-9-20160112 | SEQ ID NO: 1 KVLNGPEEEAAAPAE | without | without | 1523.765/1523.747 | 460257.3 |
| Xiedu-10-20160112 | SEQ ID NO: 1 KVLNGPEEEAAAPAE | Deamidated (N)@4 | without | 1524.67/1524.73 | 2827.23 |
| Xiedu-11-20160112 | SEQ ID NO: 1 KVLNGPEEEAAAPAE | without | without | 1523.773/1523.747 | 83587.16 |
| Xiedu-12-20160112 | SEQ ID NO: 1 KVLNGPEEEAAAPAE | without | without | 1523.758/1523.747 | 13350.15 |

TABLE 1-continued

NanoLC-ESI-MS combined MS parallel experiments in which an amino acid sequence of the SVHRP is detected out.

| Lot No | Amino Acid Sequence | Modifications | Disulfide bond | Molecular Weight Prec/Theor | Signal Intensity Precursor Signal |
|---|---|---|---|---|---|
| Xiedu-13-20160112 | SEQ ID NO: 1 KVLNGPEEEAAAPAE | without | without | 1523.763/1523.747 | 31358.74 |

Sample Lot No: xiedu 20160112-peptide summary. Txt Microsoft Excel

The SVHRP extract is treated with LaGM composite materials and subject to repeated rapid magnetic separation, and then freeze-dried. The freeze-dried polypeptide sample is redissolved in Nano-RPLC Buffer A, online Nano-RPLC liquid chromatography is performed in an Eksigentnano LC-Ultra™ 2 D System (AB SCIEX), and rinsed and desalted at a constant flow rate for 10 min. The mass spectrometry is performed using a TripleTOF 5600 system (AB SCIEX) combined with a nano-liter spray III ion source (AB SCIEX, USA), and original wiff spectrum files collected from the mass spectrometry is subject to data processing and retrieval analysis using Protein Pilot Software v. 4.5 (AB SCIEX, USA), such that the amino acid sequence of the scorpion venom heat-resistant polypeptide is detected out.

Embodiment 2

Purification of Scorpion Venom Heat-Resistant Synthesis Polypeptide by High Performance Liquid Chromatography (HPLC)

Some hybrid peptides similar to the target peptide in structure may be produced in the polypeptide synthesis process, such as diastereomers produced due to racemization of amino acids, deletion peptide produced due to un-connected part of amino acids and broken peptide produced due to the breakage of a peptide bond. Therefore, RP-HPLC is used to purify these hybrid peptides. Sample purification conditions:
Structure: KE-15
Serial No: 0200046
Lot No: P160418-CQ455216
Column: 4.6 mm*250 mm, Inertsil ODS-SP
Solution A: acetonitrile containing 0.1% trifluoroacetic
Solution B: water containing 0.1% trifluoroacetic

| Gradient: | A | B |
|---|---|---|
| 0.01 min | 10% | 90% |
| 25.00 min | 35% | 65% |
| 25.01 min | 100% | 0% |
| 30.00 min | Stop | |

Flow Velocity: 1.0 ml/min
Wavelength: 214 nm
Injection Volume: 10 μL

Embodiment 3

The Effect of SVHRSP on the Learning and Memory of AD Mice Detected by Morris Water Maze Test The water maze is used to detect behavioral changes. Place navigation experiments last 5 days, with 4 times training a day, during which the time of the mouse to find a platform (the platform is placed in the first quadrant), i.e. the escape latency, is recorded, and the mice is allowed to stay on the platform for 20 s; if the mice do not find the platform within 60 s, the escape latency is recorded as 60 s. The spatial search experiment is conducted after four times of training on the 5th day of the navigation test, the platform is removed, then the mice is placed in a pool at the entry point of the third quadrant and the test will be started. The percentage of a swimming distance to a swimming time in the target quadrant (the first quadrant) is calculated, the total duration being 60 s. The number of mice crossing the hidden platform is detected.

The Morris water maze test upon study finds that SVHRSP has a promotion effect on the spatial learning and memory ability of the AD mice. The escape latency (on the fifth day, 12±2 times) of the mice in the AD model administration group on the testing date (on the fifth day) obtained from the hidden platform of the mater maze is significantly shorter than the escape latency (**$p<0.01$) of the mice in the AD model group (on the fifth day, 22±2 times). The swimming distance is reduced from 500 cm on the 5th day of the model group to 300 cm of the administration group. By means of the platform, the times raises from 5 times in the model group into 8 times in the administration group.

Embodiment 4

Nematode Chemotaxis Testing Method

Different concentrations of SVHRSP (2, 20, 40 μg/ml) and the same amount of tri-distilled water are given to synchronized transgenic nematodes CL2355 and its control strain CL2122 respectively and administrated with drugs from the beginning of eggs, and the nematodes are transferred to a new drug-containing NGM culture dish every day. All the nematodes are incubated at 16° C. for 36 hours, the temperature of the culture dish then rises to 23° C. and the nematodes are cultured for 36 hours sequentially. The above nematodes are collected and washed three times with M9 buffer. A big dish of 100 mm is used as culture dish for the chemotaxis test. A solid medium contains 1.9% of agar, 1 mM of $CaCl_2$, 1 mM of $MgSO_4$, and 25 mM of phosphate buffer, and has a pH of 6.0. The solid medium is subjected to microwave mixing, poured into the dish and then cooled. At the bottom of the culture dish, two straight lines perpendicular to each other are drawn across the center with a mark pen, and the whole dish is divided into four quadrants. Approximately 60 nematodes in each group are placed in the center of the chemotaxic culture dish, and 1 μl of benzaldehyde (having a concentration of 0.1%, diluted with anhydrous ethanol) and 1μ of 0.25 M sodium azide are dropped into the centers of the 1 and 3 quadrants, 1 μl of anhydrous ethanol and 1 μl of 0.25 M sodium azide are dropped into the 2 and 4 quadrants, the distance from this point to the center point should be greater than 2 cm. The chemotaxis culture dish is transferred to a 23° C. incubator, and the chemotaxis index is calculated after one hour. Benzaldehyde is a high-concentration smelled chemical substance, the nematodes will be attracted by the smell of benzaldehyde, and move to the benzaldehyde area and be paralyzed in situ after exposure to sodium azide. The chemotaxis index is calculated by subtracting the number of the nematodes in the 2 and 4 quadrants from the number of nematodes in the 1 and 3 quadrants (the quadrant where attractions are located) and then dividing by the total number of the nematodes.

The SVHRSP can dose-dependently improve CI of CL2355, and 40 μg/ml of SVHRSP has an extremely protection role in neurons, and almost completely reverses the chemotactic injury induced by Aβ expression. The test result changes from control group (39.45±6.2) to administration group (7±5.66), based on the comparison of the two groups, p<0.01, which indicated that the SVHRSP could protect neurons against Aβ-induced toxic effects and improve the chemotaxis abnormity induced by neuronal Aβ expression, see Table 2.

TABLE 2

Nematode Chemotaxis Results

| Groups (μg/ml) | Average | Standard Deviation | N |
|---|---|---|---|
| Control Group | 18.25 | 1.77 | 3 |
| SVHRSP 20 | 39.45 | 6.12 | 3 |
| SVHRSP 40 | 7 | 5.66 | 3 |
| SVHRSP 80 | 10.30 | 2.406 | 3 |

Embodiment 5

Effects of SVHRSP on SH-SY5Y Oxidative Stress Induced by 6-OHDA

Fluorescent probe DCFH-DA is used to detect the effect of SVHRSP on SH-SY5Y oxidative stress induced by 6-OHDA. The experiments are divided into a normal control group, a ROSup positive control group, a 6-OHDA model group and different concentrations (2 μg/ml, 5 μg/Ml, 10 μg/ml, 20 μg/ml) of SVHRSP drug groups. SH-SY5H cells in the exponential growth phase are selected, washed with sterilized PBS after the culture solution is discarded, and then added with 0.25% trypsin to digest and blown into single cells. The cells are counted with a cell count plate, inoculated into in a 96-well plate at $1.5 \times 10^4$ cells/ml, and cultured in a incubator of 5% $CO_2$ and 37° C. for 24 h after the cells are sunk to the bottom of the plate. After 20 μg/ml SVHRSP drug group is added to intervene for 1 h, then 6-OHDA is added and continuously incubated in a incubator of 5% $CO_2$ and 37° C. for 24 h. ROSup is diluted with culture medium at a dilution ratio of 1:500, 100 μl of culture medium being added to each well. After 27 min of culture, DCFH-DA is diluted with serum-free culture medium at a dilution ratio of 1:2000 to a final concentration of 5 μmol/L, and the culture medium is discarded, 50 μl of the diluted DCFH-DA solution is added into each well, the diluted solution is gently shaken equably, and cultured in a incubator of 5% $CO_2$ and 37° C. for 20 min. The supernatant is discarded, and the cultured product is washed three times with PBS. Fluorescence detection is performed at 488 nm excitation wavelength and 525 nm emission wavelength in a fluorescence microplate reader. The OD values are measured and compared.

The ability of SVHRSP to remove active oxygen produced inside SH-SY5Y cells induced by 6-OHDA is detected by measuring ROS in the cells. The cells are given with SVHRSP (20 μg/ml) to pre-treated for 1 h, and given with 6-OHDA (100 μM) injury for 24 h, the expression of ROS in the cells is detected by fluorescence microplate reader at the excitation wavelength of 488 nm and the emission wavelength of 525 nm. The experimental results show that 6-OHDA can significantly increase the ROS in the cells, with statistical significance (control 1±0.2 vs6-OHDA 3.4±0.4 p<0.01), but when SVHRSP is added, ROS in the cells can be removed significantly, and the statistical significance (control 3.4±0.4 vs 1.5±0.4 p<0.05) can also be achieved.

Embodiment 6

The Prevention and Treatment Effects of Scorpion Venom Heat-Resistant Synthetic Peptide (SVHRSP) on Refractory Epilepsy Pilocarpine Model Rats (1) Selection and groups of animals that 180 g healthy male SD rats are selected. Lithium-pilocarpine ip (intraperitoneal administration) 300 mg/kg is used to induce temporal lobe epilepsy episodes. After 15 days of acute epilepsy episode, epilepsy rats are randomly divided into a model group and a model administration group. The animals in the epilepsy model group are administrated with intraperitoneal injection of normal saline (NS) for 15 consecutive days, the rats in the epilepsy model administration group are then divided into three model administration groups, which are administrated with ip of 50 μg/kg/d SVHRP extract, ip of 50 μg/kg/d SVHRSP, and positive control drug of sodium valproate: i.e., pilocarpine epilepsy model+NS; lithium-pilocarpine epilepsy model+SVHRP; lithium-pilocarpine epilepsy model+SVHRSP; lithium-pilocarpine epilepsy model+sodium valproate. The levels of epilepsy are observed and recorded, and graded according to Racine as the evaluation criteria.

TABLE 3

Epilepsy Episode Levels

| Level | Epilepsy Episode Statuse |
|---|---|
| 1 | Eyes closing, beard moving, facial twitching, chewing |
| 2 | Chewing aggravated with nod |
| 3 | The forelimb at one side lifts with clonicity |
| 4 | Bilateral forelimbs lift with clonicity |
| 5 | Bilateral forelimb lift with clonicity aggravated and falls |

Result Analysis:

(1) SVHRSP has a significant control effect on the chronic model epilepsy episode of lithium-pilocarpine epilepsy rats and can significantly reduce the number of episodes.

(2) SVHRSP is superior than the valproic acid group as positive control group in the reduction of the episode level and the number of episodes of the lithium-pilocarpine epilepsy rat chronic model.

Total Episode Averages superimposed ± Standard Deviation

| Days | NS n = 10 | SVHRP (50 ug/kg) n = 5 | SVHRSP (50 ug/kg) n = 5 | sodium valproate (300 mg/kg) n = 9 |
|---|---|---|---|---|
| First day | 3.78 ± 0.57 | 1.4 ± 0.6 | 0.8 ± 0.58 | 2.67 ± 0.85 |
| First two days | 6.67 ± 1.19 | 2.6 ± 0.75 | 1 ± 0.77 | 5.56 ± 1.27 |
| First three days | 9.33 ± 1.78 | 4.8 ± 1.36 | 1 ± 0.774 | 7.56 ± 1.39 |
| First four days | 11.66 ± 2.028 | 7 ± 1.94 | 1.4 ± 0.68 | 9.56 ± 1.96 |

-continued

Total Episode Averages superimposed ± Standard Deviation

| Days | NS n = 10 | SVHRP (50 ug/kg) n = 5 | SVHRSP (50 ug/kg) n = 5 | sodium valproate (300 mg/kg) n = 9 |
|---|---|---|---|---|
| First five days | 13.89 ± 2.45 | 7.2 ± 1.94 | 1.8 ± 0.86 | 11.67 ± 2.24 |
| First six days | 17.3 ± 2.64 | 9.6 ± 2.42 | 3.8 ± 0.734 | 12.67 ± 2.30 |
| First seven days | 19.89 ± 3.04 | 11.4 ± 3.09 | 5.8 ± 0.8 | 13.89 ± 2.45 |
| First eight days | 22.22 ± 3.64 | 12.6 ± 3.69 | 7.6 ± 0.87 | 15.11 ± 2.73 |
| First nine days | 23.89 ± 3.95 | 13.8 ± 3.45 | 9.4 ± 0.97 | 16.33 ± 3.05 |
| First ten days | 24.78 ± 4.04 | 15 ± 3.391 | 11 ± 1.38 | 17.55 ± 2.91 |
| First eleven days | 27.33 ± 4.21 | 16.5 ± 3.39 | 11.8 ± 1.2 | 18.89 ± 3.13 |
| First twelve days | 29.22 ± 4.78 | 19.25 ± 3.47 | 13 ± 1.14 | 20.56 ± 3.33 |
| First thirteen days | 31 ± 5.09 | 22.5 ± 4.18 | 14.6 ± 1.21 | 21.78 ± 3.58 |
| First fourteen days | 31.78 ± 5.24 | 24 ± 4.67 | 15.8 ± 1.50 | 22.67 ± 3.56 |
| First fifteen days | 32.56 ± 5.39 | 25.75 ± 5.18 | 16.6 ± 1.51 | 23.56 ± 3.79 |

Embodiment 7

Inhibitory Effect of Scorpion Venom Heat-Resistant Synthetic Peptide (SVHRSP) on Sodium Current of Primary Cultured Neurons (1) Culture of Primary Cultured Hippocampal Neurons.

An SD rat within 24 hours after birth is sterilized with 75% alcohol, broken from the heads on the ice, and hippocampuses at two sides are rapidly and completely stripped under dissecting microscope, divided into three pieces of 1 mm$^3$ in volume in dissecting solution, placed in a trypsin digestive solution with a final concentration of 0.125%, and digested in a 37° C., 10% $CO_2$ incubator for 30 min. The digested tissues are taken out, placed in a implanting fluid to stop digestion, and then subjected to mechanical blow, suspension and screen filtering to prepare a cell suspension with a density of 1×10$^5$/ml. The cell suspension is inoculated on a culture plate previously coated with polylysine (0.1 mg/ml) and incubated in a 37° C. and 10% $CO_2$ incubator. On the 2nd day, the implanting fluid is completely replaced with culture solution. On the 4th day, cytarabine (3 μg/ml) is added to the culture solution to inhibit the excessive proliferation of non-neuronal cells. 50% fresh culture solution is replaced every 3 days later. The hippocampal neurons cultured in vitro are cultured into mature neurons on the 9th to 12th days. The neurons cultured after 10 days are employed in this experiment.

(2) Whole-cell Patch-Clamp Recording.

The primary cultured hippocampal neurons are subjected to whole-cell patch clamp recording after 10 days of culture. The recording glass microelectrode has an outer diameter of 1.5 mm, an inner diameter of 0.6-0.8 mm and length of 8 cm, and is drawn with a PP-830 microelectrode drawing instrument by two-step vertical drawing. The drawn electrode has a diameter about 1 μm, and has an electrode impedance of 3-5MΩ after filled with electrode internal fluid. The reference electrode is Ag—AgCl electrode. The whole-cell patch clamp recording electrode and a cell membrane form a stable high-impedance seal therebetween, then subjected to fast capacitance compensation (C-fast), slightly applied with a negative pressure to break the membrane to form a whole-cell configuration and then subjected to slow capacitance compensation (C-slow) at a slow capacitance compensation rate of 80%-85%. Leak current is subtracted by Leak Substraction. The current activation status is observed at a set stimulus voltage. An instrument for whole-cell patch clamp recording is set that experimental parameters, data acquisition and application of stimulus of the EPC-10 dual-channel patch clamp amplifier are controlled by Pulse software, the frequency of a Bessel filter 1 being 10 KHz, and the frequency of a Bessel filter 2 being 2.9 KHz. During the course of the experiment, all the medicaments are administrated by BPS-8 perfusion device, wherein the diameter of each tube in a tube bank is 0.2 mm, and the distance between the tube orifice and the recorded cell is about 100 μm. Patch-clamp recording is performed in the primary cultured neuron system to obtain the sodium channel current, and the currents before and after the addition of the SVHRSP of the same cell are compared.

Whole-cell Patch-Clamp Recording, the currents before and after the addition of the SVHRSP of the same cell are compared, and the results show that 2 μg/ml SVHRSP could significantly inhibit the sodium channel current of the primary cultured hippocampal neurons, and the inhibition rate is over 90% (N=6) (p<0.0001). The current can be restored after being rinsed with the extracellular fluid.

Embodiment 8

Figure 11:
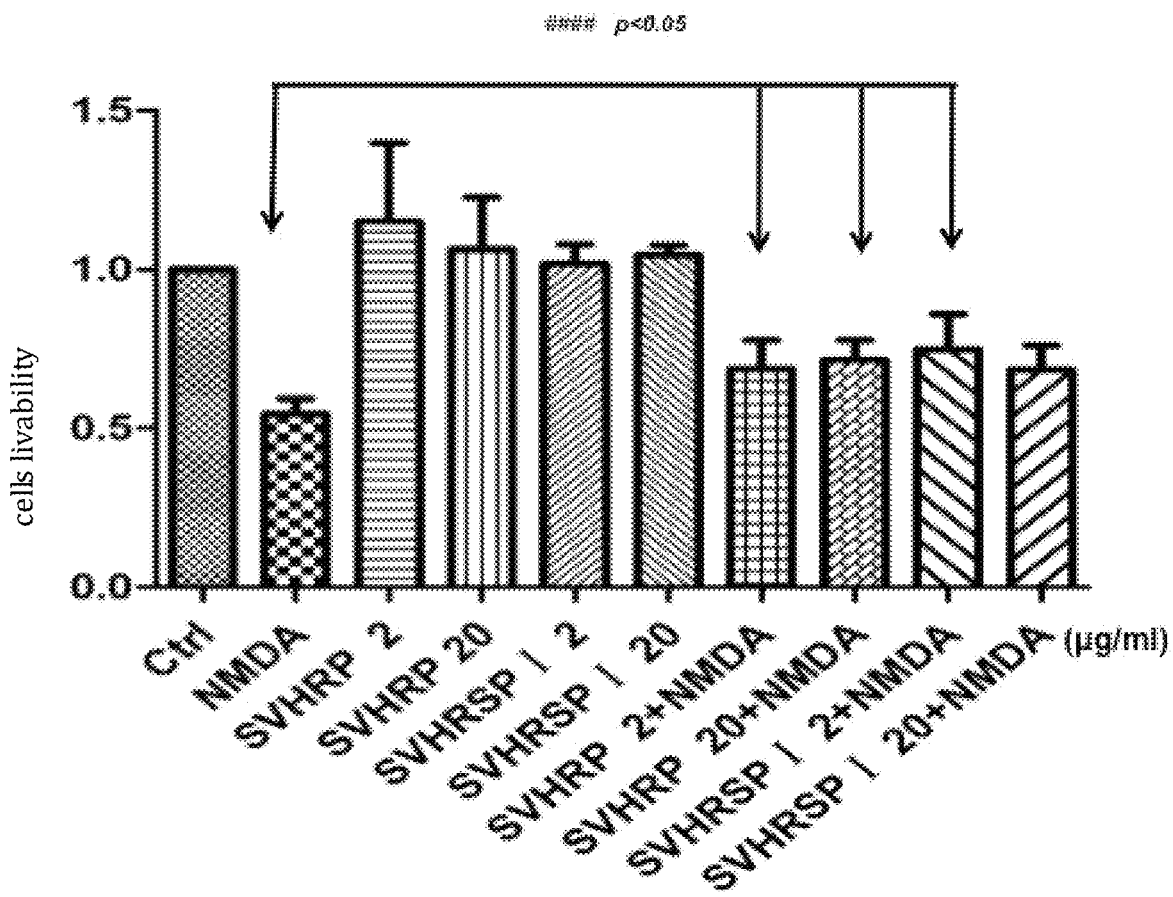
FIG. 11 shows that the SVHRSP has a Protective effect on NMDA-induced injury of SH-SY5Y cells.
Figure 12:
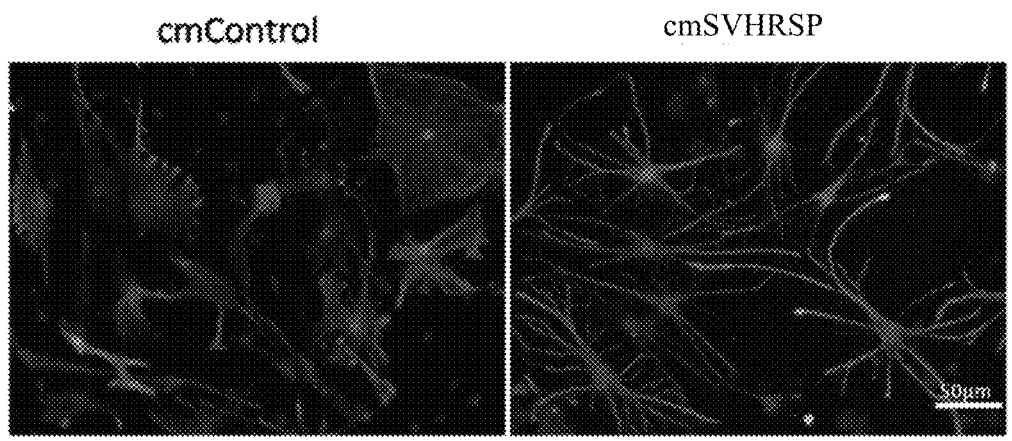
FIG. 12 shows that the SVHRSP promotes reprogramming (dedifferentiation) of type II astrocyte into neural stem cells in vitro.
Figure 13:
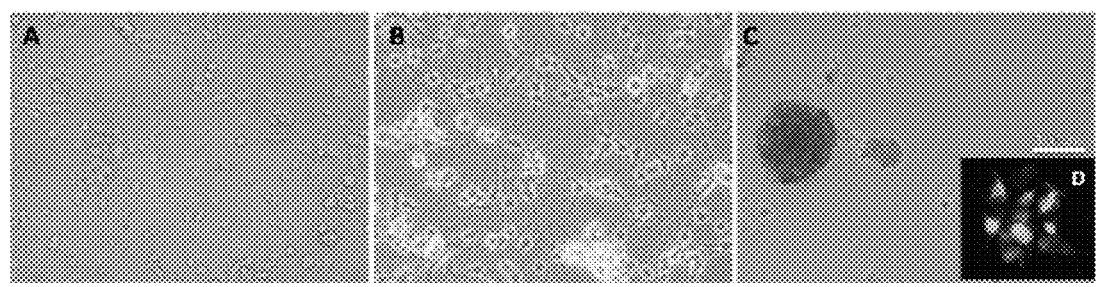
FIG. 13 shows that the SVHRSP promotes OPC cells to be dedifferentiated into neural stem cells in vitro.
Figure 14:
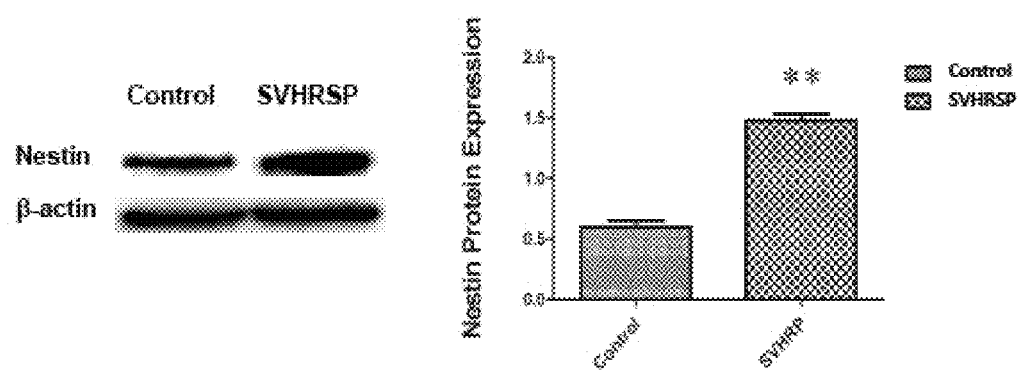
FIG. 14 shows that the SVHRSP up-regulates Nestin protein expression in de-differentiated culture cells.
Figure 15:
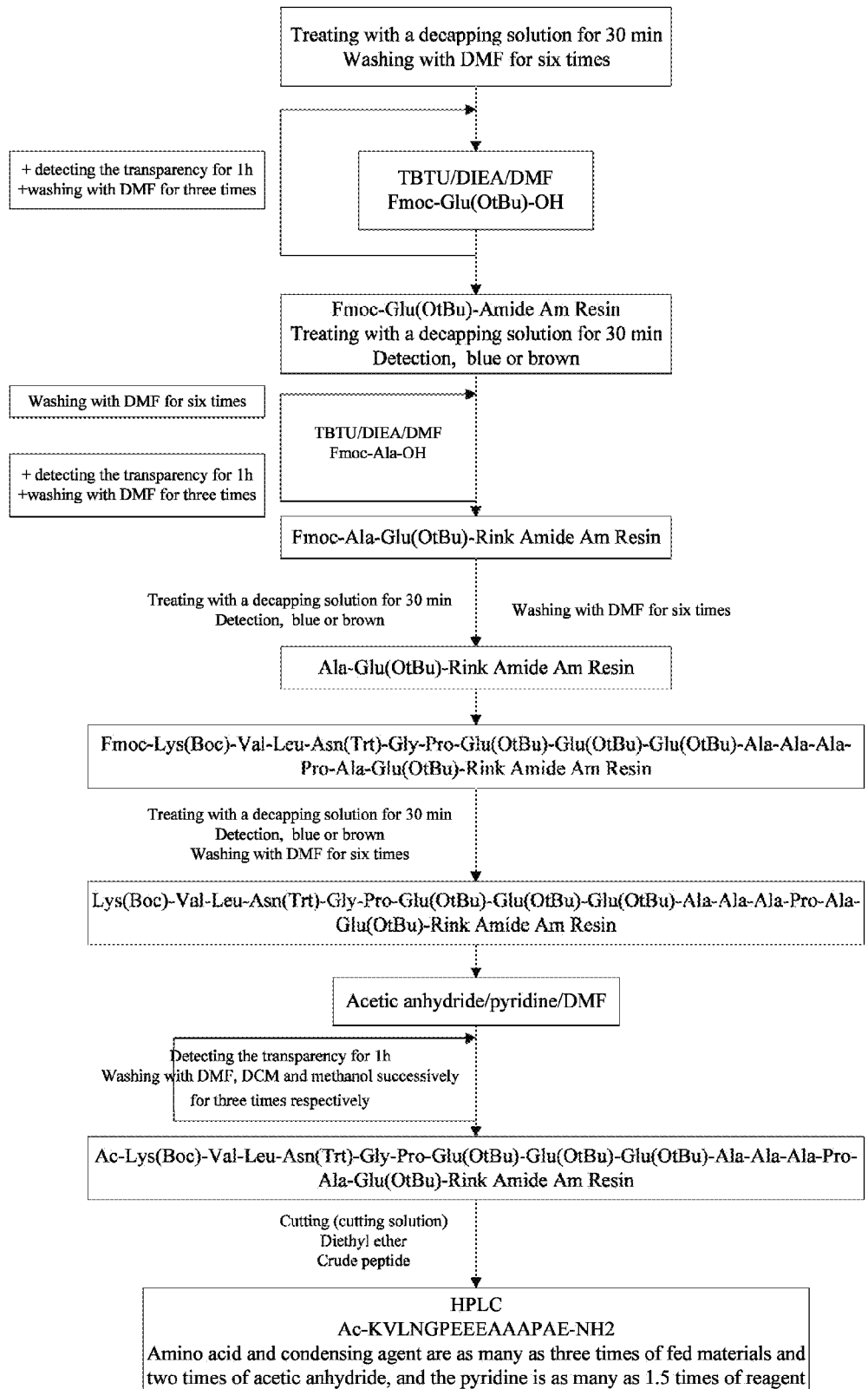
FIG. 15 shows a process for synthesizing SVHRSP.

SH-SY5Y cells are derived from human neuroblastoma cell lines. NMDA model: NMDA 20 mM+Gly 10 μM. The experimental process is as follows: before the experiment, grouping is performed according to experimental purposes. SH-SY5Y is inoculated to a 96-well plate (0.8×10$^4$/well), after 24 h added with SVHRSP and peptide preincubated for 24 h, then added with NMDA 20 mM+Gly 10 μM according to the groups and incubated for 24 h. MTT kits are used to detect the livability of various cells, see FIG. 11. The results show that SVHRSP has a protective effect on NMDA-induced injury of SH-SY5Y cells, wherein SVHRP concentration is 2 μg/ml, 20 μg/ml; SVHRSP concentration is 2 μg/ml, 20 μg/ml; NMDA: 20 mM+Gly 10 μM, p<0.05 (n=3).

Embodiment 9

Formation of Pluripotent Neural Stem Cells with Proliferation and Differentiation Abilities from Type II Astrocytes by Dedifferentiation Experimental operations: the cerebral cortex of an SD rat after 24 hours of birth is isolated aseptically and prepared into a cell suspension, primary culture of mixed glial cells is carried out in a DMEM culture solution containing 10% fetal bovine serum. After 7-9 days of culture, the product is first treated with L-leucine methyl ester hydrochloride for 1 h, and the culture solution is replaced with a fresh sterile cell culture solution, then the treated product is oscillated in a 37° C. constant temperature shaker at 18 r/min for 18 hours, the supernatant is then taken and filtered through a 200 mesh screen, the filtered supernatant is inoculated in 6-well plate treated with polylysine to obtain relatively purified OPC. The cells are naturally sunk in the incubator, whether the cells are adhered to the wall is observed after 2 hours. After the cells are adhered to the wall, the supernatant is discarded and replaced with type II astrocyte inducing fluid (20%

DMEM), and cultured for 4-5 days sequentially, then relatively purified type II astrocytes can be obtained. After 5 days, the type II astrocytes are digested and inoculated in an ultra-low adhesion 6-well plate, the culture solution is replaced with a stem cell culture solution which is then cultured for 12 days continuously, and the stem cell spheres are observed. After 12 days, the cell spheroids in the ultra-low adhesion 6-well plate are sucked out and inoculated into a 24-well plate having a polylysine-treated cell slide. After 24 h, the slide is taken out and fixed with 4% paraformaldehyde, immunofluorescence staining is performed, and Nestin (green) is used to determine whether the cell spheres are stem cells. Nestin is a specificity marker of neural stem cell, which can be used to mark the neural stem cells formed by reprogramming of type II astrocytes effected by the SVHRSP.

Embodiment 10

Acute Toxicity Test of Scorpion Venom Heat-Resistant Synthetic Peptide (SVHRSP)

1) Main Observation Indicators:

(1) Maximal tolerance dose (MTD), i.e., the highest non-lethal dose which means the highest dose that does not cause death of the tested animals;

(2) Minimal lethal dose (MLD): a dose that causes death in individual tested animals;

(3) The highest dose of nontoxic reaction (highest nontoxic dose): that is, no observed adverse effect level (MOAEL), i.e. the highest dose under which no injury is found for animals in a certain period of time;

(4) Minimum toxic reaction dose: minimum dose of toxic reaction in animals: that is the lowest dose of the toxic reaction in animals whose toxic responses are just caused.

d. Preservation conditions and preparation methods: −20° C. for long-term preservation, 4° C. for preservation within 7-10 d, and redissolved with millipore water when in use.

(3) Administration Route: respectively ip (intraperitoneal injection) route (the largest volume commonly used in mice ip route administration is 0.1-1.0 ml/20 gBW) the optimal administration doses to the animals (the doses are different, but the administration capacity is identical) are selected according to the route of administration, and 0.2 ml/20 gBW is adopted for the ip administration routes in this experiment.

(4) Selection of Employed Methods

According to the approximate lethal dose method, list the possible sequences:

the possible maximum tolerance dose and the possible minimum lethal dose of the SVHRSP are estimated according to the acute toxicity test results of the former scorpion venom heat-resistant polypeptide on Kunming mice. Then, a dose sequence table containing several doses is designed according to the 50% incremental method:

Maximal tolerance dose, MTD: 76.8, 51.2, 34.1 mg/kg

Minimal lethal dose, MLD: 115.2, 76.8, 51.2 mg/kg

The possible lethal dose ranges (115.2, 76.8, 51.2, 34.1 mg/kg) are found from the estimated dose sequence list, where each dose is given to one animal, the minimum lethal dose and the maximum tolerated dose are measured, and then the dose between the two is given to an animal. If the animal under this dose doesn't die, the range between this dose and the minimum lethal dose is the approximate lethal dose range; if the animal under this dose dies, the range between this dose and the maximum tolerance dose is the approximate lethal dose range.

TABLE 4

Detection of SVHRSP Safety by Intraperitoneal Injection Route Administration (maximum tolerance dose and minimum lethal dose)

| Administration Group | Dose | Lethal(%) | Survival (%) | Toxic Reaction |
| --- | --- | --- | --- | --- |
| BmK scorpion venom extract | 15.4 mg/kgBW | 100 | 0 | |
| BmK scorpion venom heat-resistant component extract | 15.4 mg/kgBW | 0 | 100 | 55.5 mk/kgBW iv can induce 100% death, n = 10 |
| BmK SVHRP extract | 38.4 mg/kgBW | 0 | 100 | |
| BmK scorpion venom heat-resistant polypeptide extract | 78.6 mg/kgBW | 66 | 33 | |
| SVHRSP | 78.6 mg/kgBW | 0 | 100 | No any toxic reaction is observed |
| SVHRSP | 115.2 mg/kgBW | 0 | 100 | No any toxic reaction is observed |
| SVHRSP | 172.8 mg/kgBW | 0 | 100 | No any toxic reaction is observed |
| SVHRSP | 500 mg/kgBW | 0 | 100 | No any toxic reaction is observed |
| SVHRSP | 2000 mg/kgBW | 0 | 100 | No any toxic reaction is observed |

2) Notes:

(1) Tested animals: Kunming mice, half male and half female (healthy adult, weight 19-20 g);

(2) Subjects: SVHRSP:

a. source: BmK scorpion venom extract purchased from Henan Yichang Xinxin Scorpion Factory (2012-05-28);

b. Lot No: P160418-CQ455216;

c. Content (or specification): 10 mg/piece;

The results show that the ratio of the medicinal safety and pharmacodynamic activity of the SVHRSP of the present invention are higher than 2000/0.05=40,000 times. The administration dose to Kunming mice by intraperitoneal injection route is up to 2000 mg/kg·BW and no any toxic reaction is observed. The maximum non-toxic dose (highest nontoxic dose) has not reached yet: that is, no observed adverse effect level.

We claim:

1. A method of alleviating symptoms of a neurological disease associated with amyloid beta-induced toxic effect, oxidative stress, or NMDA-induced injury, the method comprising administering to the subject a therapeutically effective amount of a pharmaceutical composition, wherein the pharmaceutical composition comprises a scorpion venom heat-resistant synthetic peptide (SVHRSP) consisting of the amino acid sequence of SEQ ID NO 1 and the neurological disease is epilepsy, Alzheimer's disease, or Parkinson's disease.

2. The method according to claim 1, wherein the neurological disease is epilepsy.

3. The method according to claim 2, wherein the subject is a human.

4. The method according to claim 1, wherein the neurological disease is Alzheimer's disease.

5. The method according to claim 4, wherein the subject is a human.

6. The method according to claim 1, wherein the neurological disease is Parkinson's disease.

7. The method according to claim 6, wherein the subject is a human.

8. A method of protecting a neuronal cell against an adverse effect, the method comprising contacting the neuronal cell with an effective amount of a pharmaceutical composition in vitro, wherein the pharmaceutical composition comprises a scorpion venom heat-resistant synthetic peptide (SVHRSP) consisting of the amino acid sequence of SEQ ID NO 1 and the adverse effect is amyloid beta-induced toxic effect, oxidative stress, or NMDA-induced injury.

9. The method according to claim 8, wherein the adverse effect is amyloid beta-induced toxic effects.

10. The method according to claim 8, wherein the adverse effect is oxidative stress.

11. The method according to claim 8, wherein the adverse effect is NMDA-induced injury.

12. A method of inhibiting the sodium channel current of a hippocampal neuronal cell, the method comprising contacting the hippocampal neuronal cell with an effective amount of a pharmaceutical composition in vitro, wherein the pharmaceutical composition comprises a scorpion venom heat-resistant synthetic peptide (SVHRSP) consisting of the amino acid sequence of SEQ ID NO 1.

* * * * *